United States Patent
Shin et al.

(10) Patent No.: US 11,224,410 B2
(45) Date of Patent: Jan. 18, 2022

(54) METHODS AND SYSTEMS FOR FILTERING ULTRASOUND IMAGE CLUTTER

(71) Applicant: KONINKLIJKE PHILIPS N.V., Eindhoven (NL)

(72) Inventors: Jun Seob Shin, Medford, MA (US); Seungsoo Kim, Andover, MA (US); Francois Guy Gerard Marie Vignon, Andover, MA (US); Sheng-Wen Huang, Ossining, NY (US); Jean-Luc Francois-Marie Robert, Cambridge, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 278 days.

(21) Appl. No.: 16/607,515

(22) PCT Filed: Apr. 24, 2018

(86) PCT No.: PCT/EP2018/060428
§ 371 (c)(1),
(2) Date: Oct. 23, 2019

(87) PCT Pub. No.: WO2018/197460
PCT Pub. Date: Nov. 1, 2018

(65) Prior Publication Data
US 2020/0138412 A1    May 7, 2020

Related U.S. Application Data

(60) Provisional application No. 62/488,904, filed on Apr. 24, 2017.

(51) Int. Cl.
*G06T 5/00* (2006.01)
*A61B 8/08* (2006.01)
(Continued)

(52) U.S. Cl.
CPC .......... *A61B 8/5207* (2013.01); *A61B 8/4488* (2013.01); *G06T 5/002* (2013.01);
(Continued)

(58) Field of Classification Search
CPC .......... A61B 8/52–5292; A61B 8/4488; G06T 5/002; G06T 7/0012; G06T 2207/10132; G06T 2207/20024; G06T 2210/32
See application file for complete search history.

(56) References Cited

U.S. PATENT DOCUMENTS

| | | | |
|---|---|---|---|
| 5,911,692 A * | 6/1999 | Hussain | B06B 1/0622 600/447 |
| 2009/0141957 A1* | 6/2009 | Yen | G01S 15/8977 382/131 |

(Continued)

FOREIGN PATENT DOCUMENTS

EP    1675064 A1    6/2006

OTHER PUBLICATIONS

Seo, et al., "Sidelobe Suppression in Ultrasound Imaging Using Dual Apodization with Cross-Correlation", IEEE Transactions and Ultrasonics, Ferroelectrics, and Frequency Control, vol. 55, No. 10, Oct. 2008, pp. 2198-2210.

(Continued)

*Primary Examiner* — Sean T Motsinger

(57) ABSTRACT

The invention provides a method for generating an ultrasound image. The method includes obtaining ultrasound data from an ultrasonic transducer array, the ultrasonic transducer array having M transducer elements. The method further includes generating N sets of image data from the ultrasound data using N random apodization functions. A minimizing function is then applied to a collection of image data, wherein the collection of image data comprises the N (Continued)

sets of image data. An ultrasound image is then generated based on the minimized image data.

14 Claims, 4 Drawing Sheets

(51) Int. Cl.
*A61B 8/00* (2006.01)
*G06T 7/00* (2017.01)

(52) U.S. Cl.
CPC .. *G06T 7/0012* (2013.01); *G06T 2207/10132* (2013.01); *G06T 2207/20024* (2013.01); *G06T 2210/32* (2013.01)

(56) References Cited

U.S. PATENT DOCUMENTS

| | | | | |
|---|---|---|---|---|
| 2012/0157851 A1* | 6/2012 | Zwirn | ................. | G01S 7/52047 600/447 |
| 2015/0324957 A1* | 11/2015 | Honjo | ..................... | A61B 8/54 600/447 |
| 2016/0019679 A1* | 1/2016 | Kesner | ..................... | G06T 5/10 382/128 |
| 2016/0089112 A1* | 3/2016 | Rosado-Mendez | .......................... | G01S 7/52042 600/442 |
| 2016/0143614 A1* | 5/2016 | Huang | ................... | A61B 8/085 600/424 |
| 2016/0192906 A1* | 7/2016 | Lee | ..................... | A61B 8/5207 600/438 |
| 2017/0245833 A1* | 8/2017 | Jensen | ................ | G01S 7/52042 |
| 2017/0363725 A1* | 12/2017 | Ignjatovic | ................ | A61B 8/14 |

OTHER PUBLICATIONS

Zemp, et al., "Imaging with unfocused regions of focused ultrasound beams", Journal of Acoustical Society of America, vol. 121, No. 3, Mar. 2007, pp. 1491-1498.
International Search Report and Written Opinion for International Application Serial No. PCT/EP2018/060428, filed Apr. 24, 2018, 17 pages.

* cited by examiner

METHODS AND SYSTEMS FOR FILTERING ULTRASOUND IMAGE CLUTTER

RELATED APPLICATIONS

This application is the U.S. National Phase application under 35 U.S.C. § 371 of International Application No. PCT/EP2018/060428, filed on Apr. 24, 2018, which claims the benefit of Provisional Application Ser. No. 62/488,904, filed Apr. 24, 2017. These applications are hereby incorporated by reference herein.

FIELD OF THE INVENTION

This invention relates to the field of ultrasound beamforming, and more specifically to the field of sidelobe clutter filtering.

BACKGROUND OF THE INVENTION

Ultrasound imaging is increasingly being employed in a variety of different applications. It is important that the image produced by the ultrasound system is as clear and accurate as possible so as to give the user a realistic interpretation of the subject being scanned. This is especially the case when the subject in question is a patient undergoing a medical ultrasound scan. In this situation, the ability of a doctor to make an accurate diagnosis is dependent on the quality of the image produced by the ultrasound system.

Off-axis and reverberation clutter signals are some of the major causes of quality degradation in ultrasound images.

Adaptive beamforming techniques, such as minimum variance (MV) beamforming, have been developed and applied to ultrasound imaging to achieve an improvement in image quality; however, MV beamforming is computationally intensive as an inversion of the spatial covariance matrix is required for each pixel of the image. In addition, even though MV beamforming is developed primarily for an improvement in spatial resolution, and is not ideal for reducing off-axis clutter, its performance in terms of improving spatial resolution often needs to be sacrificed by reducing the subarray size. Otherwise, image artifacts may occur in the speckle due to signal cancellation.

MV beamforming is also highly sensitive to phase aberration and element directivity. It is not designed to address the degradation of image quality due to reverberation clutter, which is often correlated with the mainlobe signals.

Adaptive weighting techniques, such as: the coherence factor (CF); the generalized coherence factor (GCF); the phase coherence factor (PCF); and the short-lag spatial coherence (SLSC), have been proposed but all require access to per-channel data to compute a weighting mask to be applied to the image. Further, these methods would only work for conventional imaging with focused transmit beams and are not suitable for plane wave imaging (PWI) or diverging wave imaging (DWI) involving only a few transmits.

SUMMARY OF THE INVENTION

The invention is defined by the claims.

According to examples in accordance with an aspect of the invention, there is provided a method for generating an ultrasound image, the method comprising:

obtaining ultrasound data from an ultrasonic transducer array, the ultrasonic transducer array having M transducer elements;

generating N sets of image data from the ultrasound data using N random apodization functions;

applying a minimizing function to a collection of image data, wherein the collection of image data comprises the N sets of image data; and generating an ultrasound image based on the minimized image data.

This method results in an ultrasound image with a reduced amount of sidelobe clutter. A typical medical ultrasound system will have an ultrasonic transducer array for emitting and receiving ultrasonic signals. By obtaining the received ultrasonic data from the ultrasonic transducer array, it is possible to arrange and manipulate said data to form an ultrasonic image.

An apodization function refers to a function that describes the weighting associated with individual channels of an ultrasound transducer array. The design of an apodization function is important as it determines the shape of the beampattern and therefore, the point spread function of the ultrasound system. By applying a multitude of distinct apodization functions to the ultrasound data, it is possible to generate distinct sets of image data.

Each set of image data describes a slightly different set of signals from the ultrasound imaging target. Across all of the image data sets, the mainlobe signal, which corresponds to the signal from the imaging target, will remain largely unchanged; whereas, the sidelobe signals, which correspond to the image clutter, will have a non-zero variance in their amplitude. This variance is dependent on the spatial position of the transducer element that registered the signal. In this way, some random apodization functions may result in image data sets with lower sidelobe levels. The likelihood of this occurring increases with the number of random apodization functions used.

By applying a minimizing function to the image data sets, it is possible to select image data with the lowest amplitude for a given image pixel. As the mainlobe signal remains largely unchanged across the data sets, the minimizing function will not substantially change the mainlobe signal. On the other hand, as the sidelobe signals vary across the image data sets, the minimization function will select image data with the lowest sidelobe signal amplitude across all of the image data sets for a given image pixel. In this way, the sidelobe clutter signals of an ultrasound image are substantially reduced, whilst leaving the mainlobe signal intact.

The resulting ultrasound image, generated from the minimized data, is a high contrast ultrasound image with significantly reduced clutter signals.

In an embodiment, the N random apodization functions operate on P random elements of the M transducer elements, wherein P is less than or equal to M.

The random apodization functions act on a given number of transducer elements within the transducer array, meaning that P random elements will be active and the remainder, M-P, will be inactive. In this way, the N image data sets will have very similar mainlobe signals and very different sidelobe signals, associated with reverberation and off-axis clutter. By accentuating the difference in sidelobe signals between image data sets, thereby increasing the variance in sidelobe amplitude, the likelihood of at least one data set having low amplitude sidelobe signals increased. This in turn leads to increasing the effectiveness of the minimizing function in reducing the sidelobe clutter in the final ultrasound image.

In a further embodiment, the value of P changes for each random apodization function.

By changing the number of random elements operated on for each random apodization function, the variance of the sidelobe signal amplitudes is increased. In this way, the effectiveness of the minimizing function in reducing the sidelobe clutter in the final ultrasound image may be further increased.

In another embodiment, the value of P is selected based on the focusing quality of the ultrasound data.

In situations where the focusing quality of the ultrasound data is low, such as imaging in the near-field or in the cases of PWI or DWI with only a small number of plane- or diverging-wave transmits, the number of random elements activated by the random apodization function is increased. Typically, the lower the number of active random elements, the higher the mean amplitude and variance of the sidelobe signals.

In an arrangement, the same sequence of N random apodization functions is used for each generation of an ultrasound image.

In this way, it is possible to use a predetermined sequence of random apodization functions, rather than having to generate new functions for each cycle of ultrasound image generation. By using a predetermined sequence of random apodizations functions, it is possible to apply a previously tested set of random apodization functions, leading to more predictable results in the final image.

In some arrangements, the N random apodization functions are selected based on patient information.

Part of the ultrasound data may contain information regarding the target being imaged. For example, the information may include a target imaging area or a physical attribute of the patient.

In an embodiment, the N random apodization functions are derived from Q independent apodization functions, wherein Q is less than N.

In this way, the ultrasound system is not required to store a large number of random apodization functions. By deriving apodization functions from a few initial functions, the storage requirements of the ultrasound system are reduced.

In some designs, the N random apodization functions are complex-valued functions.

By utilizing complex-valued random apodization functions, it is possible to introduce a steering effect to the received signals. In this way, the lateral resolution of the final ultrasound image may be improved.

In an arrangement, the method further comprises:
applying a rectangular apodization function to the ultrasound data, thereby generating a rectangular set of image data.

In a further arrangement, the collection of image data further comprises the rectangular set of image data.

By applying a rectangular function to the ultrasound data, it is possible to generate standard B-mode ultrasound image data.

In an embodiment, the method, before the step of applying the N random apodization functions, further comprises coherently compounding the ultrasound data.

In this way, the filtering method may be applied to ultrafast ultrasound imaging systems utilizing plane wave imaging (PWI) or diverging wave imaging (DWI).

In some arrangements, the method, further comprises:
performing a log compression of the ultrasound image;
applying a spatial low pass filter to the ultrasound data;
applying a spatial low pass filter to the ultrasound image;
generating a detail component of the ultrasound data by subtracting the spatial low pass filtered ultrasound data from the ultrasound data; and
combining the detail component of the ultrasound data with the spatial low pass filtered ultrasound image.

In this way, it is possible to improve the spatial resolution of the ultrasound image to match that of the ultrasound data, resulting in a clutter free, high contrast, high resolution ultrasound image. In addition, this method may help to match the image brightness and speckle variance to the ultrasound data, which may have been degraded by the minimizing function.

According to examples in accordance with an aspect of the invention, there is provided a computer program comprising computer program code means which is adapted, when said computer is run on a computer, to implement the method described above.

According to examples in accordance with an aspect of the invention, there is provided an ultrasound system comprising:
an ultrasonic transducer array having M transducer elements, wherein the ultrasonic transducer array is capable of emitting and receiving ultrasonic signals;
a signal processor for compiling the received ultrasonic signals into an ultrasound image; and
a controller, wherein the controller is adapted to:
obtain ultrasound data from an ultrasonic transducer array, the ultrasonic transducer array having M transducer elements;
generate N sets of image data from the ultrasound data using N random apodization functions;
apply a minimizing function to a collection of image data, wherein the collection image data comprises the N sets of image data; and
generate an ultrasound image based on the minimized image data.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method for generating an ultrasound image. The method includes obtaining ultrasound data from an ultrasonic transducer array, the ultrasonic transducer array having M transducer elements. The method further includes generating N sets of image data from the ultrasound data using N random apodization functions. A minimizing function is then applied to a collection of image data, wherein the collection of image data comprises the N sets of image data. An ultrasound image is then generated based on the minimized image data.

Figure 1:
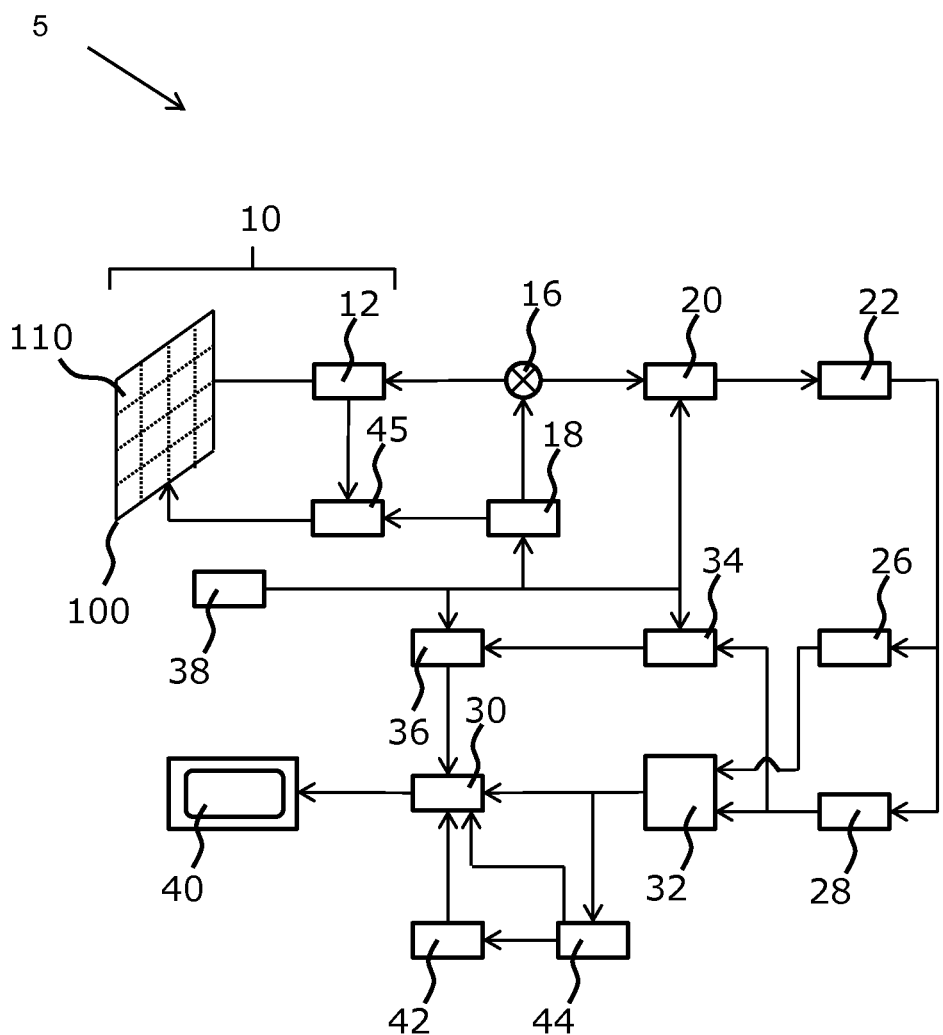
FIG. 1 shows an ultrasound diagnostic imaging system to explain the general operation.

The general operation of an exemplary ultrasound diagnostic imaging system will first be described, with reference to FIG. 1, and with emphasis on the signal processing function of the system since this invention relates to the processing and filtering of the signals measured by the transducer array.

The system comprises an array transducer probe 10 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The transducer array 100 is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasound beams from the transducer array 10 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducers are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 10' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 10' and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
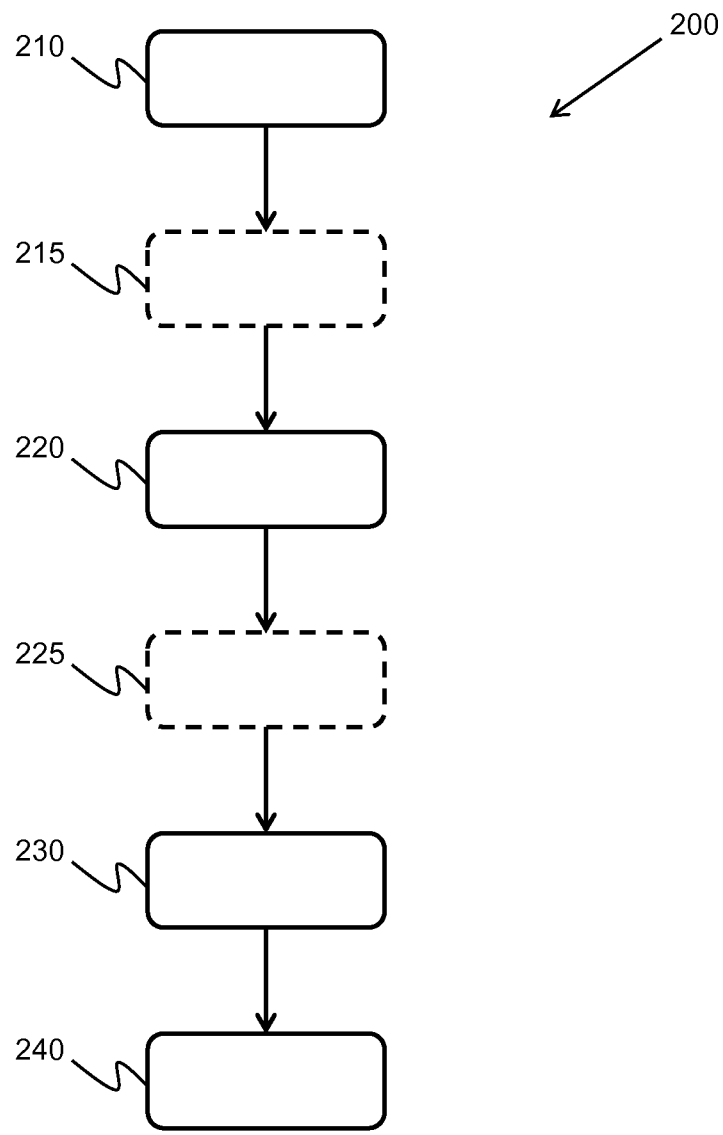
FIG. 2 shows a method of the invention.

FIG. 2 shows a method 200 for generating an ultrasound image.

The method begins in step 210 by obtaining ultrasound data from an ultrasonic transducer array, the ultrasonic transducer array having M transducer elements. Each of the M elements of the ultrasonic transducer array will produce channel data.

The method may then progress to step 215, wherein the ultrasound data is coherently compounded. Coherent compounding of the ultrasound image data improves both the lateral resolution and signal to noise ratio of the data.

In step 220, N sets of image data are generated from the ultrasound data using N random apodization functions. Each of the N random apodization functions are distinct, leading to N different sets of image data.

For conventional delay-and-sum (DAS) beamforming with a rectangular apodization function, we can express the beamsum signal, or the beamformer output, y(x,z) at the spatial location (x,z) as:

$$y(x,z)=s(x,z)+\Sigma_i c(x_i,z),$$

where s(x,z) is the on-axis, mainlobe signal and $c(x_i,z)$ is the off-axis, sidelobe clutter signal from the $i^{th}$ off-axis scatterer. This equation may further be expressed as:

$$y(x,z)=s(x,z)+\Sigma_i BP(x_i,z)r(x_i,z),$$

where BP $(x_i,z)$ is the beampattern at the location of the $i^{th}$ off-axis scatterer and $r(x_i,z)$ is the reflectivity of the $i^{th}$ off-axis scatterer.

Similarly, when N different realizations of random apodization functions are used, we have:

$$y_k(x,z)=s_k(x,z)+\Sigma_i c_k(x_i,z), k=1,2,\ldots N,$$

where $y_k(x,z)$, $s_k(x,z)$, and $c_k(x_i,z)$ are the beamformer output, the on-axis signal, and the off-axis clutter signal from the $i^{th}$ off-axis scatterer, respectively, from the $k^{th}$ realization of the N random apodization functions. Again, the off-axis clutter signal $c_k(x_i,z)$ can be expressed as a product between the beampattern and the reflectivity of the off-axis scatterer as shown below:

$$y_k(x,z)=s_k(x,z)+\Sigma_i BP_k(x_i,z)r(x_i,z)$$

Across the N sets of image data, the mainlobe signal $s_k(x,z)$ will remain largely unchanged; however, the sidelobe signals $c_k(x_i,z)$ will have a non-zero variance. This variance is dependent on the spatial location of the transducer elements that registered the signal. In this way, some random apodization function may result in lower sidelobe levels. The likelihood of this occurring increases with the number of random apodization functions used.

The N random apodization functions may operate on P random elements of the M transducer elements, wherein P is less than or equal to M. This leads to P transducer elements being active and the remainder being inactive. For example, for an ultrasonic transducer array having 64 transducer elements, 50 random apodization functions may be applied to the collected ultrasound data where only 32 random elements are operated on by each random apodization function. As the sidelobe variance is dependent on the spatial locations of the transducer elements, using the apodization functions to randomly select elements to activate leads to an increase in the variance. This in turn increases the likelihood that, for each pixel of the final image, at least one of the image data sets will have a low sidelobe amplitude.

The variance in sidelobe amplitude may be further increased by changing the value of P for each random apodization function. For example, in the first random apodization function, 32 transducer elements may be active; whereas, in the second random apodization function, 26 transducer elements may be active. Alternatively, the same number of transducer elements may be active for all random apodization functions.

The number of random elements, P, may be selected based on the focusing quality of the ultrasound data. When ultrasound imaging is performed in the near-field region or when only one way focusing is available, such as in ultrafast ultrasound systems employing PWI or DWI, the focusing quality of the imaging data is low. In these cases, the number of random elements activated for each apodization function may be increased in order to reduce the average sidelobe amplitude. This may help to distinguish the sidelobes from the mainlobe in cases where the low focusing quality results in on and off-axis signals being of a similar shape.

The same sequence of N random apodization functions may be used for each generation of an ultrasound image. Rather than generating a new set of N random apodization functions for each image generation cycle, it may be possible to store and reuse the same apodization functions for a number of cycles. For example, the same 50 random apodization functions may be used for an entire ultrasound imaging procedure for a patient over multiple image generation cycles. The functions may also be stored for the next procedure, or a new set of 50 functions may be generated.

Information on the patient may be used to generate the N random apodization functions. For example, if the target of the ultrasound is the heart, it may be indicated to the ultrasound system that the ribs may cause a substantial amount of scattering and image clutter. In response to this, the apodization functions may act to activate the central elements of the transducer array and leave the outer elements, those closest to the ribs, deactivated.

The N random apodization functions may be derived from Q independent apodization functions, wherein Q is less than N. For example, 5 random apodization functions may act as master functions from which 50 random apodizations may be derived through routine variations.

The N random apodization functions may also be complex-valued functions. Complex-valued functions may be used to introduce a steering effect to the beams formed by the ultrasonic transducer array. This may help to improve the lateral resolution of the ultrasound image as well as the contrast.

In step 225, a rectangular apodization function may be applied to the ultrasound data, thereby generating a rectangular set of image data. In this case, the collection of image data further comprises the rectangular set of image data.

For a rectangular apodization function, the image data will have a lower average sidelobe amplitude compared to the random apodization functions; however, due to the non-zero variance of the sidelobe amplitudes from the image data sets generated using the random apodization functions, for a given location it is likely that at least one of the image data sets will have a lower sidelobe amplitude than the rectangular image data set. By introducing a rectangular function, a failsafe sidelobe amplitude is established as, even in the case where every image data set generated by the random apodization functions has higher sidelobe amplitudes than the rectangular image data set, the minimizing function will select the rectangular image data set. This ensures a minimum level of final ultrasound image quality is attained during every ultrasound image generation cycle.

In step 230, a minimizing function is applied to the collection of image data comprising the N sets of image data and, in some cases, the rectangular set of image data.

To obtain the minimum values of the data sets, we have:

$$\min_k \{y_k(x, z)\} = \min_k \left\{ s_k(x, z) + \sum_i BP_k(x_i, z) r(x_i, z) \right\}$$

Since the mainlobes, or on-axis signals, from the different random apodization functions remain virtually unchanged, we let $s_k(x,z) \approx s(x,z)$ and obtain the following expression:

$$\min_k \{y_k(x, z)\} = s(x, z) + \min_k \left\{ \sum_i BP_k(x_i, z) r(x_i, z) \right\}$$

This equation suggests that taking the minimum of the N different image data sets, i.e.

$$\min_k \{y_k(x, z)\},$$

is equivalent to finding the beampattern that minimizes the off-axis clutter signal, or sidelobes, for a given spatial location (x,z).

In step 240 an ultrasound image is generated based on the minimized image data. The minimized data will have a reduced level of off-axis clutter signals, or sidelobes, meaning that the ultrasound image will have a higher contrast.

Figure 3:
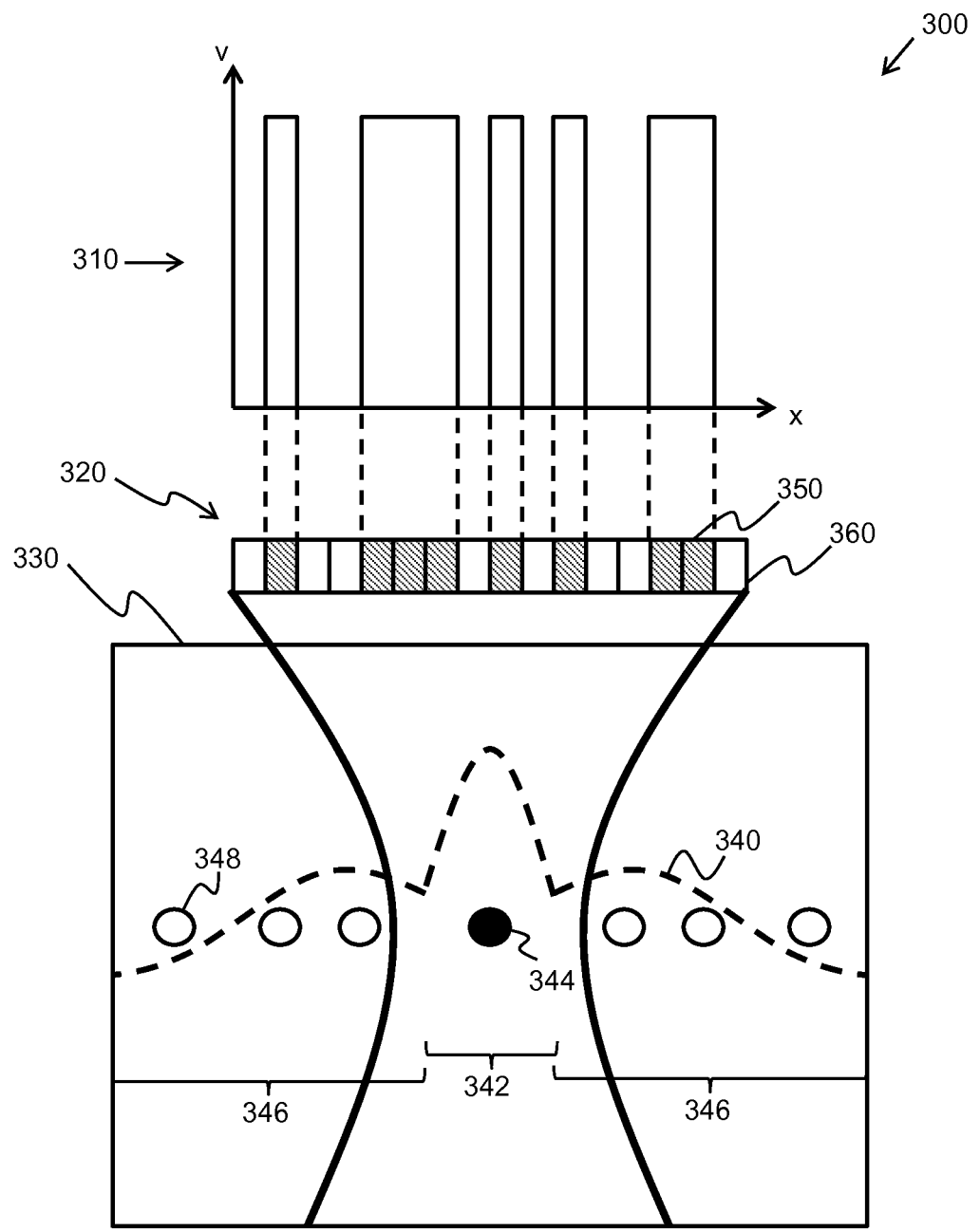
FIG. 3 shows an illustrative example of a method of the invention.

FIG. 3 shows an illustrative example 300 of a random apodization function 310 applied to a transducer array 320, the transducer array having 16 transducer elements. The random apodization function is plotted as voltage weighting, v, against transducer number, x.

The transducer array receives signals from a targeted field of view 330. The signals are combined into a beamsum signal 340, shown by the dashed line. The beamsum signal can be described as a sum of the on-axis mainlobe signal 342, s(x,z), originating from the imaging target 344, and the off-axis sidelobe signals 346, $c(x_i,z)$, originating from off-axis scatterers 348 in the field of view.

In this case, the apodization function 310 operates on 8 of the transducer elements causing them to behave as active elements 350, leaving the remaining elements to act as deactivated elements 360. For each of the N random apodizations used random transducer elements will be activated and deactivated. This will introduce a large variance to the clutter signals 346 across the image sets; however, the mainlobe signal 342 will remain largely unchanged.

In practice, some of the transducer elements of the transducer array may be physically blocked. If the blocked elements are known by the ultrasound system, the random apodizations function may take this into account when selecting which elements to activate. In this way, the random apodization function can prevent the blocked elements from being activated.

Figure 4:
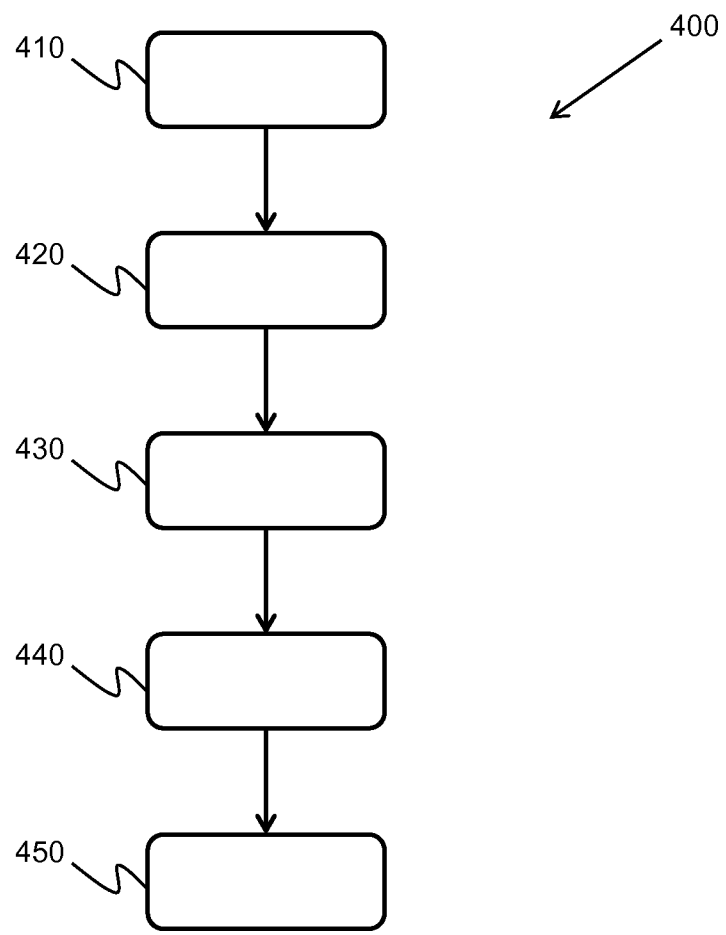
FIG. 4 shows a further method which may be used within the method of FIG. 2.

FIG. 4 shows a further method 400, which may occur within the method of FIG. 2. The minimization involved in the filtering method described in FIG. 2 often introduces a blocky, low resolution appearance to the high contrast image, which may be overcome by the following process.

In step 410, a log compression is performed on the ultrasound image. The variation in the amplitude of radio frequency data collected by an ultrasound system is very high. Typically, the image data is mapped to a 0-255 gray scale image; however, many of the important tissue structures have image values of 0-9. This may result in high amplitude points overshadowing the rest of the image. By performing log compression on the image, it is possible to generate a more balanced image.

In step 420, a spatial low pass filter is applied to the ultrasound data, which may be written as: $LPF(I_0)$ where $I_0$ is the ultrasound data; and in step 430, a spatial low pass filter is applied to the ultrasound image, which may be written as: $LPF(\min(I_1, I_2, \ldots, I_N))$ where $I_2$ is the second image data set and $I_N$ is the $N^{th}$ image data set. These two steps are the initial stages in decomposing the high resolution, low contrast first image data and the low resolution, high contrast filtered ultrasound image into their constituent parts.

In step 440, a detail component of the ultrasound data is generated by subtracting the spatial low pass filtered ultrasound data, obtained in step 420, from the original ultrasound data. This may be written as: $D_0 = I_0 - LPF(I_0)$. $D_0$ is the detail component and contains the high resolution, low contrast information from the ultrasound data.

In step 450, the detail component may be combined with the spatial low pass filtered ultrasound image, obtained in step 430, which contains the low resolution, high contrast information. This is given by the following equation: $I_{final} = LPF(\min(I_1, I_2, \ldots, I_N)) + D_0$ where $I_{final}$ is the final high resolution, high contrast ultrasound image. In this way, it is possible to benefit from the enhanced contrast in the filtered image, whilst preserving the smoothness and detail from the original ultrasound data.

In addition to matching the spatial resolution of the filtered image to the original image, this method may also match the image brightness and speckle variance of the filtered image to the original image. The filtered image tends to show increased variance in speckle and appear darker than the original image because the minimum operation reduces the global brightness of the image. This is more pronounced in clutter or anechoic regions and less pronounced in the speckle or the mainlobe.

As discussed above, embodiments make use of a controller for performing the data processing steps.

The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for generating an ultrasound image, the method comprising:
   obtaining ultrasound data from an ultrasonic transducer array, the ultrasonic transducer array having M transducer elements;
   generating N sets of image data from the ultrasound data using N random apodization functions, wherein the N random apodization functions are derived from Q independent apodization functions, wherein Q is less than N;
   applying a minimizing function to a collection of image data, wherein the collection of image data comprises the N sets of image data; and
   generating an ultrasound image based on the minimized image data.

2. A method as claimed in claim 1, wherein the N random apodization functions operate on P random elements of the M transducer elements, wherein P is less than or equal to M.

3. A method as claimed in claim 2, wherein the value of P changes for each random apodization function.

4. A method as claimed in claim 2, wherein the ultrasound data is obtained in the obtaining step by focused transmit beam imaging, plane wave imaging, diverging wave imaging, or near field imaging, and further wherein the value of P is selected based on the obtaining step.

5. A method as claimed in claim 1, wherein the same sequence of N random apodization functions is used for each generation of an ultrasound image.

6. A method as claimed in claim 1, wherein the N random apodization functions are selected based on a target being imaged.

7. A method as claimed in claim 1, wherein the N random apodization functions are complex-valued functions.

8. A method as claimed in claim 1, wherein the method further comprises:
   applying a rectangular apodization function to the ultrasound data, thereby generating a rectangular set of image data.

9. A method as claimed in claim 8, wherein the collection of image data further comprises the rectangular set of image data.

10. A method as claimed in claim 1, wherein the method, before the step of applying the N random apodization functions, further comprises coherently compounding the ultrasound data.

11. A method as claimed in claim 1, wherein the method, further comprises:
   performing a log compression of the ultrasound image;
   applying a spatial low pass filter to the ultrasound data;
   applying a spatial low pass filter to the ultrasound image;
   generating a detail component of the ultrasound data by subtracting the spatial low pass filtered ultrasound data from the ultrasound data; and
   combining the detail component of the ultrasound data with the spatial low pass filtered ultrasound image.

12. A computer program product embodied in a non-transitory computer-usable medium, comprising computer program code which is adapted to implement the method of claim 1.

13. A controller for generating an ultrasound image in an ultrasound system, wherein the controller is adapted to:
   obtain ultrasound data from an ultrasonic transducer array, the ultrasonic transducer array having M transducer elements;
   generate N sets of image data from the ultrasound data using N random apodization functions, wherein the N random apodization functions are derived from Q independent apodization functions, wherein Q is less than N;
   apply a minimizing function to a collection of image data, wherein the collection image data comprises the N sets of image data; and
   generate an ultrasound image based on the minimized image data.

14. An ultrasound system comprising:
   an ultrasonic transducer array having M transducer elements, wherein the ultrasonic transducer array is capable of emitting and receiving ultrasonic signals;
   a signal processor for compiling the received ultrasonic signals into an ultrasound image;
   a controller as claimed in claim 13; and
   an image output device for outputting the filtered ultrasound image.

* * * * *